United States Patent [19] [11] 4,021,102
Iizuka [45] May 3, 1977

[54] AUTO-REFRACTOMETER

[75] Inventor: Tadashi Iizuka, Machida, Japan

[73] Assignees: Kabushiki Kaisha Hoya Lens; Kabushiki Kaisha Sokkisha, both of Tokyo, Japan

[22] Filed: Sept. 27, 1974

[21] Appl. No.: 510,127

[30] Foreign Application Priority Data

Nov. 26, 1973 Japan ............................ 48-132340

[52] U.S. Cl. .................................... 351/13; 351/6; 356/128
[51] Int. Cl.² ..................... A61B 3/10; G10N 21/48
[58] Field of Search ........... 351/6, 13, 14; 250/206, 250/216; 356/128

[56] References Cited

UNITED STATES PATENTS

| 2,049,222 | 7/1936 | Reason | 351/13 X |
| 2,114,984 | 4/1938 | Reason | 351/6 |
| 3,536,383 | 10/1970 | Cornsweet et al. | 351/6 |
| 3,824,005 | 7/1974 | Woestman | 351/13 X |

OTHER PUBLICATIONS

Allen et al., "An Infra-Red...Mechanism," Amer. J. Opt. & Such Amer. Acad. Opt., vol. 37, pp. 403–407, 1960.
Roth, "Automatic...Eye," Review of Sci. Inst., vol. 36, No. 11, pp. 1636–1639, Nov. 1965.
Warshawsky, "High...Accomodation," JOSA, vol. 54, No. 3, Mar. 1964, pp. 375–379.
Campbell et al., "High...Optometer," JOSA, vol. 49, No. 3, Mar. 1959, pp. 268–272.

Primary Examiner—Paul A. Sacher
Attorney, Agent, or Firm—Cushman, Darby & Cushman

[57] ABSTRACT

An auto-refractometer according to this invention comprises a light beam source for producing a measuring ray wherein beams from a pair of invisible infrared ray emission diodes are alternately flickered, and real images of the beams are converged on respective sides of ridges at the output side of a V-shape coincidence prism at positions close to the ray axis thereby reducing the horizontal distance between the beams. A measuring optical system includes a transmitting collimater which projects said measuring ray passing through a vertical slit to permit focusing of a slit image on the retina. A receiving collimater collects beams reflected from the cornea and the retina, and by a semi-transparent mirror, and directs them via a reflection mirror to an interference bar which interferes with the beam from the cornea. A split prism divides the beam received from the retina, and a pair of elements photoelectrically convert the divided beam into electrical outputs. An electrical circuit includes a movable mechanism integrally associated with a lens system to focusing the image reflected from the retina on said split prism. The circuit produces high-speed flickering of the infrared ray emission diodes and responds to differential outputs from the photo-electric elements to cause said movable mechanism to move by an amount corresponding to the refractory diopter of the eye.

6 Claims, 5 Drawing Figures

AUTO-REFRACTOMETER

BACKGROUND OF THE INVENTION

1. Field of the Invention

This invention relates to a device for automatically measuring the refractory diopter of the eyes, and more particularly relates to a auto-refractometer to permit the automatic measuring of the refractory diopter of the eyes using invisible infrared rays as measuring rays and providing instantaneous indication of diopter in the form of digital data.

2. Description of the Prior Art

To optically measure eyes, there are two methods - one utilizing information provided by the person being tested and the other using external measuring devices.

In practising the first method, a device such as a vision tester has been widely applied for many years, but such a device provides no accurate measurement because of self-consciousness of the testee, and such a device also requires considerable floor space for measuring. Also, only a specialized optical engineer can measure the refractory diopter.

To practice the second method, considerable skill is necessary for measurement, and presently measuring accuracy is low because of an effect on the eyes of strong measuring rays projected thereon.

SUMMARY OF THE INVENTION

By contrast, according to the present invention, measuring error is substantially eliminated by means of a correction mechanism even through the testee moves his eye axis and blinks during measuring. Consequently, correct results are always obtained. Furthermore, since invisible infrared rays are employed as measuring rays, the adjusting mechanism of the eyes is not activated. A target is automatically positioned at clearly visible distance corresponding to the refractory diopters of the eyes during normal observation, and refractory diopters under very natural conditions are obtained as one of the advantages over conventional testing methods.

An auto-refractometer according to this invention comprises a light beam source for producing a measuring ray wherein beams from a pair of invisible infrared ray emission diodes are alternately flickered, and real images of the beams are converged on respective sides of ridges at the output side of a V-shape coincidence prism at positions close to the ray axis thereby reducing the horizontal distance between the beams. A measuring optical system includes a transmitting collimator which projects said measuring ray passing through a vertical slit to permit focus of a slit image on the retina. A beam receiving collimator collects reflected beams from the cornea and the retina, and by a semi-transparent mirror and directs them via a reflection mirror to an interference bar which interferes with the beam from the cornea. A split prism divides the beam received from the retina, and a pair of elements photo-electrically convert the divided beam into electrical outputs. An electrical circuit includes a movable mechanism integrally associated with a lens system to focus the image reflected from the retina on said split prism (.) The circuit produces high-speed flickerng of the infrared ray emission diodes and responds to differential outputs from the photo-electric elements to cause said movable mechanism to move by an amount corresponding to the refractory diopter of the eye.

BRIEF DESCRIPTION OF THE ACCOMPANYING DRAWINGS

FIG. 1 is a diagram showing the entire optical system of a preferred embodiment of to this invention, FIG. 2 is an elevational view of an image rotating reflection mirror, FIG. 3 is a side elevational view of an arrangement including three image rotating reflection mirror devices, FIG. 4 is a diagram schematically illustrating the testing of two eyes, and FIG. 5 is a block diagram of an electrical control circuit, which includes a computer forming part of the invention.

DESCRIPTION OF THE PREFERRED EMBODIMENTS

A preferred embodiment of the auto-refractometer according to this invention will be hereinafter discussed referring to the accompanying drawings, wherein there are illustrated: a complete optical system, including a light beam source, a measuring optical system, an image rotating reflection mirror, and automatic ray axis correction means; a movable mechanism for changing the position of optical elements and an auto-control electric circuit are illustrated.

Figure 1:
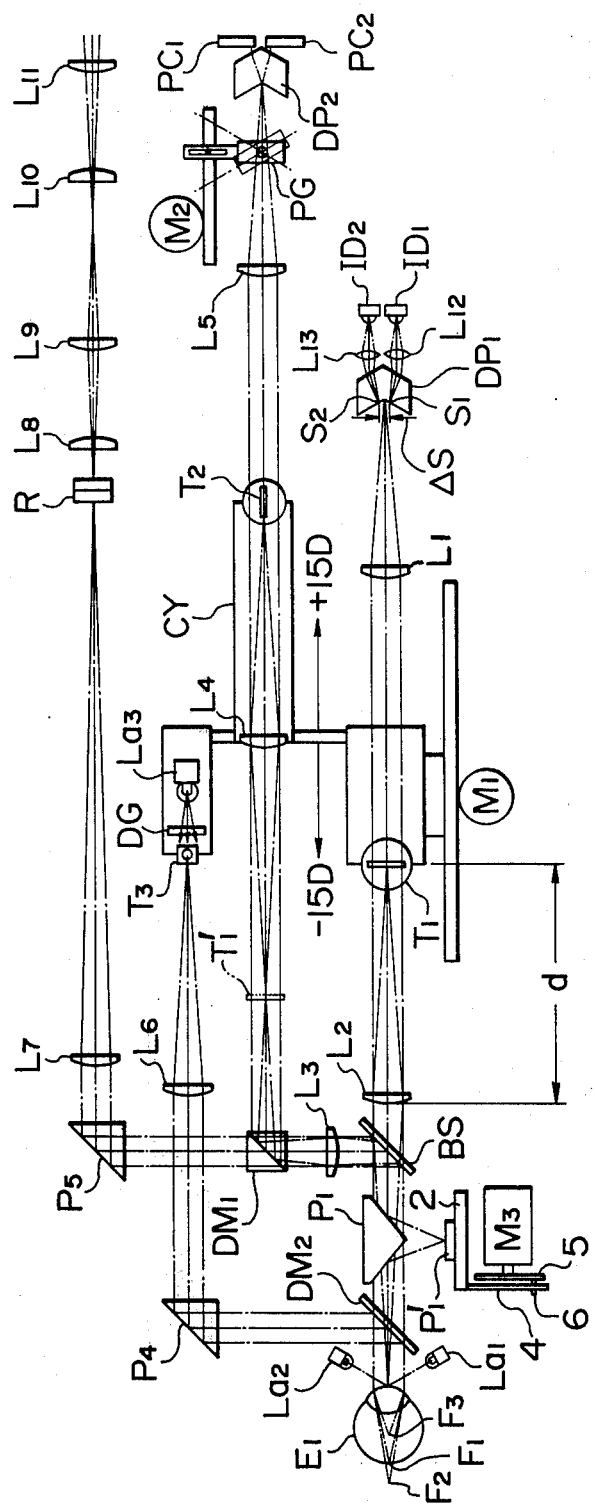

FIG. 1 shows a complete optical system, wherein a light beam source comprises infrared ray emission diodes $ID_1$ and $ID_2$ symmetrically located above and below a measuring axis. The beams from the diodes are collected at lenses $L_{12}$ and $L_{13}$, and after passing said lenses, said beams are compactly focussed with a gap ($\Delta S$) of 1mm at ridges on the output side of the coincidence prism $DP_1$. Images $S_1$, $S_2$ of the beam source are realized on symmetrical positions of said ridges of the prism. In FIG. 1, the pair of ray emission diodes are shown above and below the measuring axis for the convenience of the explanation, but actually, they are placed in a line perpendicular to the drawing.

Figure 5:
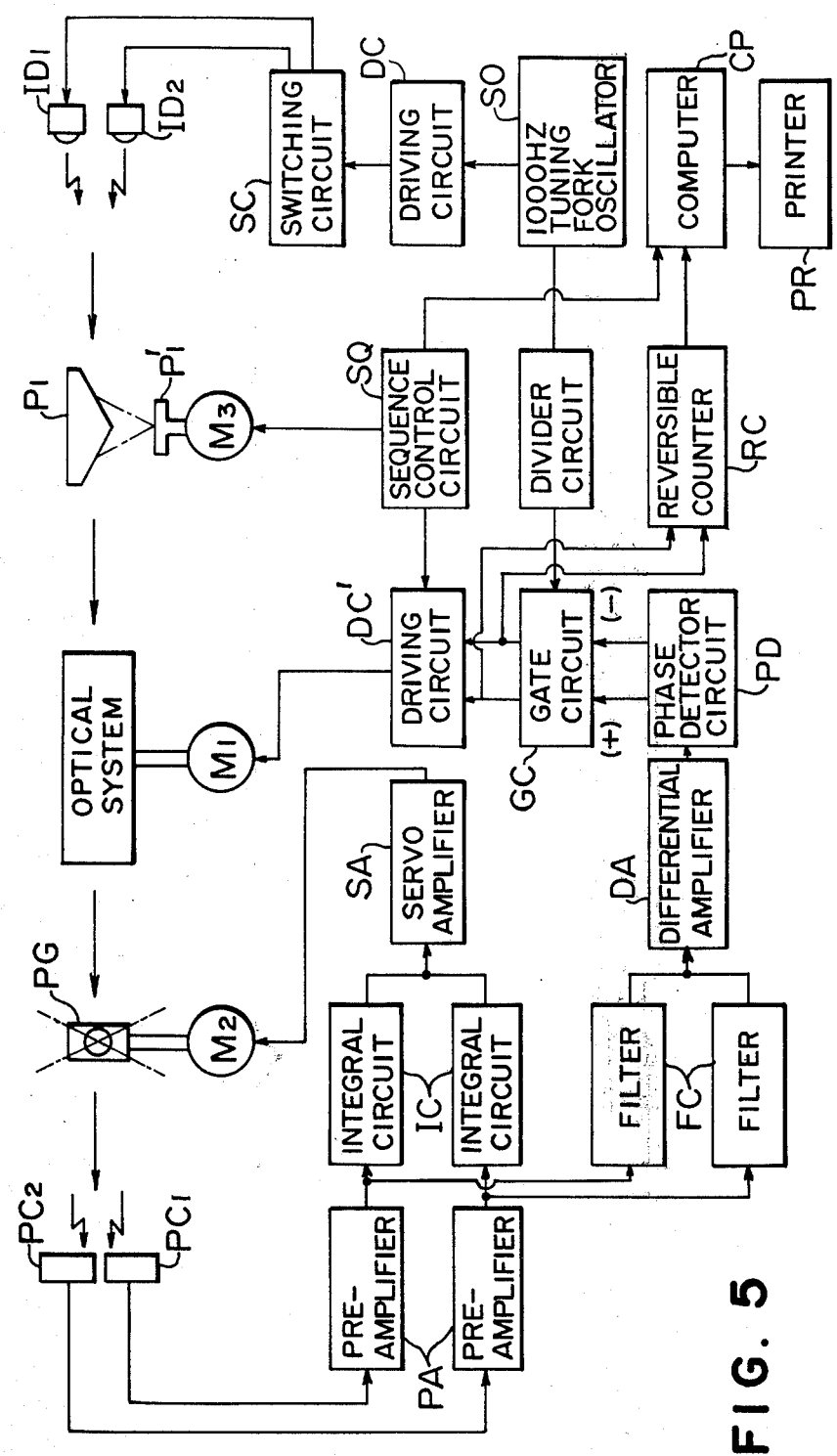

The ray emission diodes produce outputs having a wave length of 0.9 microns (invisible infrared rays), the rays being flicker-modulated alternately at 1,000 Hz by means of the switching circuit in FIG. 5 (using 260 mw). Rays emanating from the light beam source pass through a lens $L_1$ ($f_1 = 45$ mm) and are directed to an elongated slit $T_1$ as nearly parallel pencils of light.

The beam passes through the slit $T_1$ diposed behind a ray transmitting collimator lens $L_2$ ($f_1$=62.5mm) and passes through 2 to become parallel pencils of light (with respect to the normal eye of $D_3$=0), which are received on the eye via a semi-transparent mirror BS and an image rotating reflection mirror $P_1$, $P'_1$.

When the pupil of the eye receiving incident light is placed at a focal surface in front of the collimator $L_2$ to view the slit $T_1$, images are directed thereto by both $S_1$ and $S_2$.

When the refractory diopter of the eye is normal, the slit images projected by $S_1$ and $S_2$ are focussed at a point $F_1$ on the retina, and the images are reflected by a system comprising semi-transparent mirror BS beam receiving collimator $L_3$ ($f_3$ =62.5 mm) and dichroic mirror DM, to produce an image $T'_1$, which is static with respect to the switching of the beam source.

The image $T'_1$ passes through relay lenses $L_4$, $L_5$ and is symmetrically focussed as an image of $T_1$ on the ridges on both sides of the split prism $DP_2$. The beam is evenly divided and is projected on the photo-electric elements $PC_1$, $PC_2$, thereby to be photo-electrically converted as indicated in FIG. 5.

However, when the eye is myopic or hyperopic, the slit images projected by $S_1$ and $S_2$ are focused at points $F_3$ or $F_2$, respectively, and the image $T'_1$ is displaced and oscillated on opposite sides of that position of $T'_1$ shown in FIG. 1 which repesents the image location for an emmetropic eye.

When the position of the slit $T_1$ is moved with respect to the ray axis, the incident light from the slit $T_1$ is diverged or converged to thereby focus on $F_2$ or $F_3$. Moving the position of the slit $T_1$ rearward or forward to focus on the retina the reflection image becomes static. As described hereafter, a servo mechanism is controlled to automatically focus the slit image on the retina.

To provide corrections in cases where ray axis matching is incomplete and the slit image of the reflected beam from the retina of the eye examined is displaced asymmetrically with respect to the ridges of the split prism $DP_2$, etc., an automatic correction device is provided. This device comprises a servo mechanism and a parallel plane glass PG obliquely rotatable with respect to the ray axis and located intermediate the lens $L_5$ and the split prism $DP_2$. The slit image of the reflection beam being displaced asymmetrically, the outputs of the pair of the photo-electric elements $PC_1$, $PC_2$ provide a DC difference which actuates the servo motor $M_2$ to cause the parallel glass PG placed in the convergence optical system to be obliquely inclined, thereby moving the beam path so as to automatically correct the variation of the ray axis from the eye, so that an always correct measurement is provided in a manner that the image is symmetrically focussed with respect to the ridges of the split prism $DP_2$. To this end, the slit image is long enough in lengthwise direction, so that the output is not affected and the correction is accomplished perpendicularly to the lengthwise direction of said slit.

The relative relationship of the refractory diopter $D_e$ and the displacement value d of slit $T_1$ from lens $L_2$ is given in the following formula;

$$D_e = \frac{1}{f_2}\left(1 - \frac{d}{f_2}\right)$$

where $f_2$ is a focal distance ($f_2$ =62.5 mm) of the beam transmitting collimator lens $L_2$, and $D_e$ is in units of diopter, where the unit is $m$.

Where d = 5mm, $$D_e = \frac{1}{0.0625}\left(1 - \frac{0.005}{0.0625}\right) = +15 \text{ diopters}$$

Where d = 120 mm, $$D_e = \frac{1}{0.0625}\left(1 - \frac{0.120}{0.0625}\right) = -15 \text{ diopters}$$

That is, the whole stroke of the slit $T_1$ is 120 − 5 = 115mm, whereby the measuring of ±15 diopters is possible.

In order to move the perpendicular slit $T_1$ within the range of possible measurement (± 15D in this case) from the normal position of the eye (D=0), a movable member (integrally associated with relay lens $L_4$ a target $T_3$, and its illuminating member), is automatically moved forwardly and rearwardly by means of a motor $M_1$ controlled by the differential outputs of $PC_1$, $PC_2$. If markings for the possible measuring range (±15D in this embodiment) are provided around the normal eye position ($D_e$=0), direct reading of the diopter is possible according to the variable value of the displacement of $T_1$.

Compared to light from the retina, the reflection light reflected from the cornea is very strong. Since the latter rides on that from the retina, the signal to noise ratio (S/N) becomes very low, thereby presenting a problem of low accuracy of the photo-electric detection. In order to eliminate photo-electric signals caused by noise, there is provided a beam interference bar $T_2$. When the cornea is on the focal plane in front of the beam projecting collimator $L_2$, the image of the beam source is focussed as a real image on both sides, of the center of the cornea. Light reflected from the cornea becomes a parallel ray after passing the receiving collimator $L_3$, and it then is reflected at the dichroic mirror $DM_1$, whereby images of the beam source $S_1$ and $S_2$ are focused side by side at the center of the focal plane of the relay lens $L_4$. Therefore, with the beam interference bar $T_2$ having its horizontal narrow width located perpendicular to the ray axis on the focal plane of $L_4$, $T_2$ serves as a noise trap and almost all of the cornea reflection light is eliminated. The signal reflection beam from the retina passes bar $T_2$ as a parallel ray, the amount of interference by the interference bar being only a few percent, a substantially negligible amount.

As described above, the slit $T_1$ moves automatically corresponding to the refractory diopter of the eye, by means of the movable member. The other slit image $T'_1$, focussed by the beam receiving collimator, having a same focal distance as that of the beam projecting collimator, moves on the ray axis a distance corresponding to that of slit $T_1$. Therefore, tubular cylinder CY is arranged integrally with said lens $L_4$ and said interference bar $T_2$ to permit focusing of the reverse image of $T'_1$ on the ridges of the split prism $DP_2$.

In the above described arrangement, there is shown only of refractory diopter on the meridian plane perpendicular to a slit projected to determine refractory diopter. However, this invention also permits simultaneous measurement of the refractory diopter of astigmatism and astigmatism axis of the eye in one test.

To accomplish this the projection of the slit $T_1$ is directed to, for example, three meridian planes thereby permitting measurement of the refractory diopters thereof. The data developed is used for analyzing the functional formula of the total refractory diopters including astigmatism of the eye, whereby the spherical refractory diopters of the astigmatism and astigmatism axis are computed simultaneously and are displayed in a printed form, or as a digital indication by a computer.

Letting the refractory diopters measured at three meridian plane directions be $X_1$, $X_2$, $X_3$, respectively, the data of the refractory diopters of the eye can be calculated from the following formula:

$$X = a + b \sin(2 + \alpha)$$

wherein a cylindrical focal distance (astigmatism) $b$ is complexed with the spherical focal distance $a$, the directional angle of the cylindrical axis with respect to the horizontal axis is $\alpha$, the meridian angle rotated from the horizontal axis is $\theta$, and the focal distance focused with a slit image on the meridian plane is X. With the values of $\theta$ and X being determined, $a$, $b$ and $\alpha$ are calculated.

The focal distances $X_1$, $X_2$, $X_3$ where $\theta$ are 0°, 60°, 120° are calculated from the following formulas.

$$X_1 = a + b \sin \alpha \ldots \quad (1) \text{ or } X_1 - a = b \sin \alpha \ldots (1')$$

$$X_2 = a + b \sin(120° + \alpha) \ldots \quad (2)$$
$$\text{or } X_2 - a = b \sin(120° + \alpha) \ldots \quad (2')$$

$$X_3 = a + b \sin(240° + \alpha) \ldots \quad (3)$$
$$\text{or } X_3 + a = b \sin(240° + \alpha) \ldots \quad (3')$$

Adding (1), (2), and (3) and $a = 1/3 (X_1 + X_2 + X_3)$ is obtained wherein $a$ is an arithmetic mean. Adding the formulas (1'), (2') and (3') after they are squared, then $$b = \frac{1}{1.5} \sqrt{(X_1 - a)^2 + (X_2 - a)^2 = (X_3 - a)^2}$$

then deducting (3') from (2'), and eliminating by comparison as to $b$, $$\tan \alpha = \frac{\sqrt{3} \times (X_1 - a)}{X_2 - X_3}$$

from which $\alpha$ is calculated.

Figure 2:
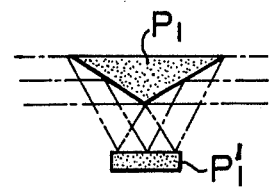
Figure 3:
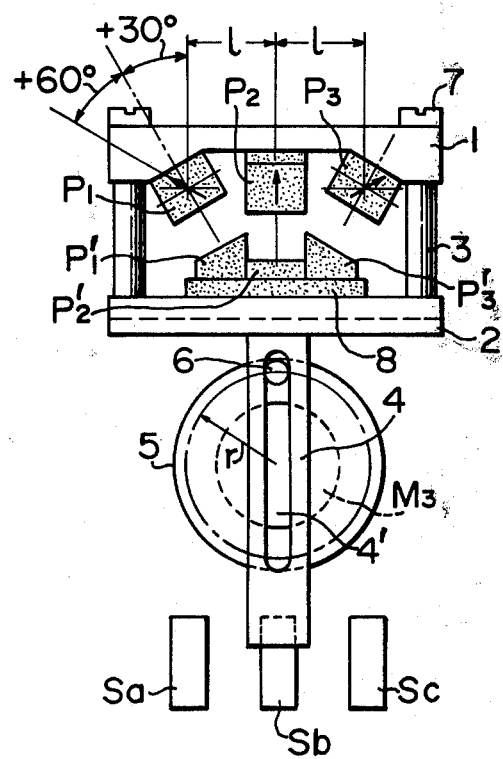

A mechanism for step changing the meridian plane of the incident light is explained referring to FIG. 2 and 3.

A meridian rotating device is located in the optical path between the semi-transparent mirror BS (separating the beam projecting optical system from the beam receiving optical system) and the eye, as shown in FIG. 1. The image rotating reflection mirror comprises a plurality of compound mirrors arranged in pairs. Describing one pair, a reflection mirror $P_1$ has two-reflection surfaces and a reflection mirror $P'_1$ has one reflection surface as shown in FIG. 2, the latter being securely fitted on the horizontally movable sliding base 2 as shown in FIG. 3. The ray axis of each reflection mirror is different. More particularly, $P_2$ is vertical while $P_1$ and $P_3$ are on opposite sides of $P_2$ at +30° and −30°, respectively. The upper reflection mirrors $P_1$, $P_2$, $P_3$ are fixed on the supporting frame 1 which is secured to said sliding base 2 by pillars 3. The lower reflection mirrors $P'_1$, $P'_2$, $P'_3$ are secured on the glass base 8 with the same inclinations as the corresponding upper reflection mirrors, said glass base being secured on the sliding base 2.

The image rotating mirrors are mounted horizontally and are spaced by the distance $\iota$. Any of $P_1$, $P_2$, $P_3$ may be selectively brought into the path of the image bearing rays by moving the arm 4 of the sliding base 2.

In order to permit the automatic selection of the ray axis, a pin 6 vertically mounted at the periphery of a disc 5, fixed to the shaft of a driving motor $M_3$, is slidably engaged within an elongated slot 4' provided in the center of the arm 4. Rotation of the disc produces movement of arm 4 causing the image rotating mirrors to be relatively positioned.

In FIG. 3, $Sa$, $Sb$, $Sc$ are contactless switches for controlling the above pin and also for supplying positional signals of the meridian measured to the computer shown in FIG. 5.

With the image rotating reflection mirror arranged as above, when a perpendicular slit image is projected to the image rotating reflection mirror $P_1$ (with −30° ray axis) the output ray axis is received in the eye after rotating 60°, i.e. twice 30°.

The reflection beam from the retina returns through the same path by means of the image rotating reflection mirror, is then rotated, and is returned to perpendicular direction. The ray axis of $P_2$ being perpendicular, the incident light into the eye is only reversed, whereby the meridian remains perpendicular without having any directional rotation. The ray axis of $P_3$ having a −30° inclination, the meridian is −60°, so that the three meridian planes are established by three image rotating reflection mirrors.

Thus, if one measures at least three meridian planes, the correct and accurate $b$ and $\alpha$ for the eye measured are obtained.

The advantages of the auto-refracto meter employing said image rotating reflection mirrors reside in that there is no need of rotating the beam transmitting optical system, the beam receiving system and the electromechanical device; and the reflected image returns to the original perpendicular condition by itself without requiring rotation of the reflection image for restoration. The only rotation is that of the incident light into the eye. Therefore, according to this application of the image rotating reflection mirrors, not only is the total device simplified, but it also provides the advantage of causing no errors or tolerance to the angular positions of the meridian planes, even the some tolerance exists in the moving position, because the image rotating reflection mirrors are fixed at the meridian planes with the rotary angles three times dividing the circle.

Reflection mirror $DM_1$ shown in FIG. 1, is a dichroic mirror reflecting the infrared rays but passing 90% of visible rays. When the eye is illuminated by lamps $La_1$, $La_2$, the reflected beams from the pupil pass through $DM_1$, said beams also passing through the objective lens $L_7$ and cross line R, so that the measurer can match the optical ray axis of the measuring optical system to the pupil center very correctly and accurately with the aid of the erecting lenses $L_8$ - 11.

Furthermore, the semi-transparent dichroic mirror $DM_2$ shown in FIG. 1 passes the infrared rays while reflecting one half and passing the other of the visible rays, whereby the testee can align himself to match the ray collimating axis and the ray axis by watching a target $T_3$ through collimator $L_6$. The target $T_3$ is a selected pattern which is easily seen, against a weakly lit member DG made of an opal glass and illuminated by light passing from lamp $La_3$ through a green filter.

However, when the testee watches such target, the self adjusting mechanism of the eye functions thereby providing an incorrect refractory diopter of the eye. As a first step towards eliminating this, the target $T_3$ linked with the slit $T_1$ automatically is positioned to measure a refractory diopter a little larger than that of the actual diopter measured by the device, the eye watching target being positioned farther from the eye by −1.0D.

Furthermore, as the two eyes of the testee will be in better adjusting condition if they are both in use rather than that of the one eye being used, the testee watches the targets $T_3$ and $T'_3$ with both eyes as shown in FIG.

Figure 4:
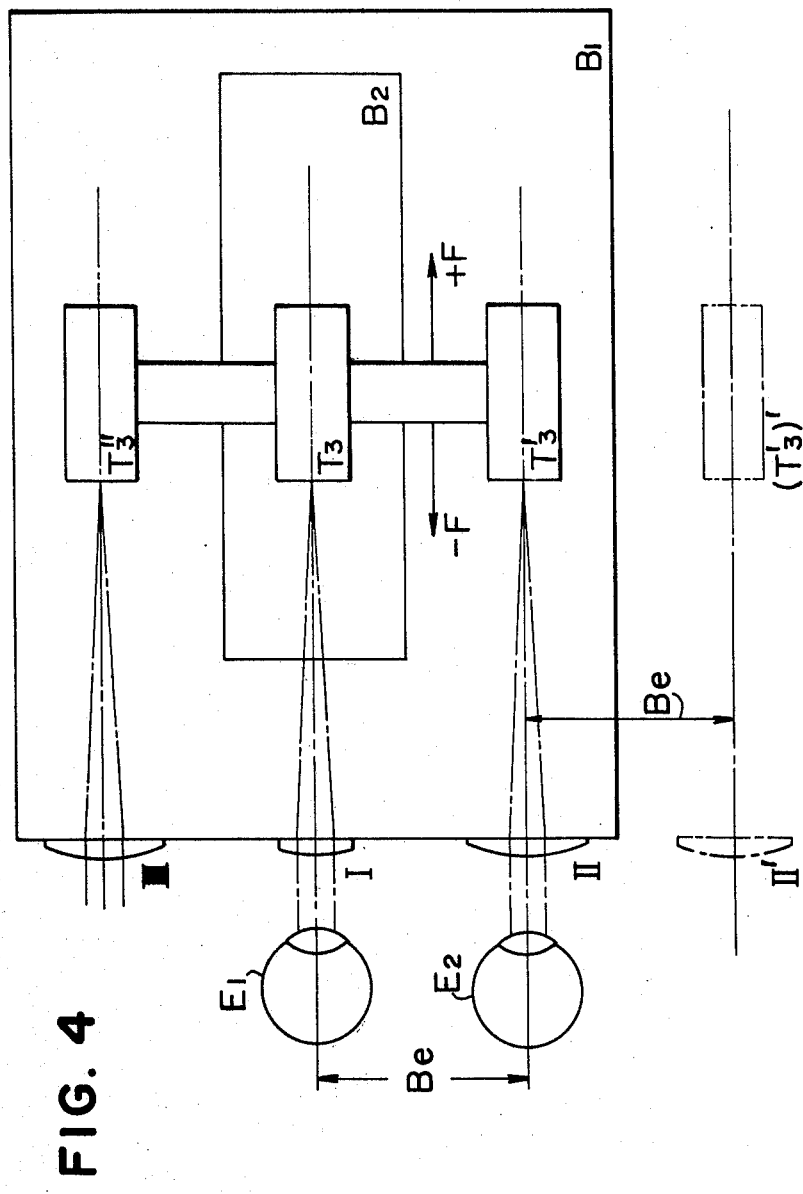

4. In FIG. 4, Be is the distance between the eyes $E_1$ and $E_2$ and a spacing Be is maintained between $T_3$, $T'_3$, $T''_3$ the targets being horizontally and axially movably mounted on the movable member.

In FIG. 4, three optical systems I, II and III include collimators (corresponding to $L_6$). Targets $T_3$, $T'_3$, $T''_3$ are arranged on carriage $B_2$ to automatically adjust the distances between the targets and the collimators simultaneously. When the left eye $E_1$ as measured, the testee watches the collimator I with his left eye $E_1$ as shown. To test the right eye, $E_2$, the whole device $B_1$ is moved by the inter-eye distance Be, (as shown by II in the drawing, so the testee can watch the collimator of system I with his right eye $E_2$, while watching the collimator of system III with his left eye $E_1$. In order to apply this device to variable inter-eye distances Be of different testees, the effective distances between the optical systems is arranged to be adjustable, so that the testee can watch the target more easily.

The electric system now will be discussed referring to FIG. 5.

The both right and left ray emission diodes $ID_1$ and $ID_2$, alternately flicker by receiving rectangular positive and negative AC current waves via a driving circuit DC and a switching circuit SC from a 1000 Hz tuning fork oscillator SO. The photo-electric beam receiving elements $PC_1$, $PC_2$ have maximum sensitivity at 0.9 micron wave length, wide beam receiving square and high sensitivity, and produce a low noise signal.

The outputs of $PC_1$ and $PC_2$ are amplified by a preamplifier PA having a low noise characteristic. The DC components of the amplifier outputs are passed through an integral circuit IC, are amplified by a servoamplifier SA, and then are supplied to servo-motor $M_2$ for automatically controlling the ray axis. The AC components of the amplifier outputs are passed for improved S/N ratio through narrow band filter circuits FC, then are differentially amplified by a differential amplifier DA, and thereafter are phase detected by a phase detector PD to thereby develop positive or negative directional discriminating signals applied to a gate circuit GC. Pulse signals from the tuning fork oscillator SO are divided and are also applied to the gate circuit. The gate output is directed via a driving circuit DC' to a pulse motor $M_1$ to complete the focal point control servo-circuit.

The pulse motor $M_1$ is located at zero position prior to the beginning of the measuring, and the transition time from zero to ± 55mm is one second. The pulse motor rotates one revolution per 48 pulses, whereby the targets can be moved 56.5mm in one revolution of a pinion, the diameter of which is 18mm. Consequently, when the pulse motor shaft and the pinion shaft are coupled by gears having a reduction ratio of 1 : 6.25 and the output from the tuning fork oscillator SO after passing the divider circuit is 300 Hz pulse frequency, the targets can be moved 55mm per second.

The distance moved by the slit $T_1$ is calculated by counting by means of a reversible counter the number of pulses supplied to pulse motor $M_1$. In order to calculate the refractory diopters and axial direction of the astigmation, the slit directions are separately counted in three directions of 0°, 60°, 120° for every 60° and are stored.

Directional conversions and each of the three directional countings of the slit are controlled by a sequence control circuit SQ, wherein the control of action by signal interruptions caused by the blinking of the testee, automatic return or reset upon the termination of the measurement, calculation by a computer, printing indication PR, etc. are all automatically controlled.

Although the invention has been shown and described with respect to a preferred embodiment thereof, it should be understood by those skilled in the art that various changes and omissions in the form and detail thereof may be made therein without departing from the spirit and the scope of the invention.

I claim:

1. An auto-refractometer for measuring diopter of a patient's eye, comprising:

means for producing a beam of measuring rays, said means including a pair of spaced infrared ray emission diodes, a V-shaped coincidence prism arranged with respect to said diodes to converge rays emitted by said diodes towards a beam path, and means for alternately driving said diodes;

an optical system including a beam transmitting collimator for projecting said beam through a slit to said eye to be focussed on the retina and reflected by the retina and cornea, reflection means for directing the beam reflected from said eye through a receiving collimator towards an interference bar oriented to interfere with that portion of the reflected beam reflected by said cornea, a split prism for dividing the reflected beam from said retina which passes the interference bar, and a pair of photoelectric elements respectively responsive to the divided portions of said reflected beam to produce electrical outputs;

a movable mechanism operatively related to said optical system; and circuit means responsive to differences between said electrical outputs for actuating the movable mechanism to thereby move said optical system by an amount corresponding to the diopter of the eye.

2. An auto-refractometer as set forth in claim 1, further comprising optical correction means interposed between the interference bar and the split prism for altering the reflected beam passing the interference bar thereby causing the reflected beam to impinge symmetrically on the split prism.

3. An auto-refractometer as set forth in claim 1, further comprising a target operatively related to said movable mechanism and visible to both eyes of the patient to permit alignment of an eye with said projected beam.

4. An auto-refractometer as set forth in claim 1, wherein said optical system further comprises an image rotating mirror arrangement interposed between said eye and the reflection means, said rotating mirror arrangement having a plurality of reflecting surfaces and being movable so as to change stepwise the meridian plane of an image of the slit carried by the projected beam.

5. An auto-refractometer as set forth in claim 4 wherein said circuit means includes a computer responsive to diopter measured in each of the meridian planes for calculating spherical focal distance of the eye, spherical refractory diopter of astigmatism and astigmatism axis.

6. An auto-refractometer as set forth in claim 4, wherein said circuit means comprises a pair of preamplifiers each connected at its input to respective outputs from said photoelectric elements, and preamplifiers being joined at their outputs to respective integral circuits and to respective filters;

a phase detector circuit connected to the outputs from said filters;

an oscillator;

a divider circuit joining said ocillator to an input of a gate circuit, said gate circuit being interposed between outputs of said phase detector circuit and an input to a driving circuit;

a sequence control circuit joined to an input of the driving circuit for controlling the operation thereof;

a motor connected to the output of said driving circuit, said motor being joined to the movable mechanism to actuate said mechanism upon energization of the motor by said driving circuit;

an additional motor for moving said image rotating mirror arrangement, said additional motor being joined to an output of said sequence control circuit;

a reversible counter connected between the outputs of said gate circuit and an input to a computer, said computer also having as an input thereto an output from said sequence control circuit whereby said computer operates under the control of the control circuit and in response to diopter measured in each of the meridian planes to calculate spherical focal distance of the eye, spherical refractory diopter of astigmatism and astigmatism axis;

and a switching circuit joined to said diodes, said switching circuit being connected via an additional driving circuit to an output from said oscillator whereby said diodes are alternately driven.

* * * * *